United States Patent [19]

Serhan et al.

[11] Patent Number: 5,079,261

[45] Date of Patent: Jan. 7, 1992

[54] USE OF LIPOXIN A4 AND ITS DERIVATIVES AS ANTAGONISTS FOR SLOW-REACTING SUBSTANCES OF ANAPHYLAXIS

[75] Inventors: Charles N. Serhan, Brookline, Mass.; Kamal Badr, Nashville, Tenn.

[73] Assignee: Brigham and Women's Hospital

[21] Appl. No.: 344,633

[22] Filed: Apr. 28, 1989

[51] Int. Cl.$^5$ ............................................. C09F 7/00
[52] U.S. Cl. ................................................... 514/552
[58] Field of Search ........................................ 514/552

[56] References Cited

U.S. PATENT DOCUMENTS 4,560,514 12/1985 Samuelsson et al. ............... 260/410
4,576,758 3/1986 Morris .............................. 260/405.5

OTHER PUBLICATIONS

Scott, R. H. et al., Nature, 330:760-762 (1987).
Benowitz, N. L., Annu. Rev. Med., 41:277-288 (1990).
Samuelsson, B. et al., Science, 237:1171-1176 (1987).
Serhan, C. N. et al., Proc. Natl. Acad. Sci. USA, 81:5335-5339 (1984).
Dahlen, S. E. et al., Acta Physiol. Scand., 130:643-647 (1987).
Dahlen, S. E. et al., Adv. Exper. Med. Biol., 229:107-130 (Chapter 9), 1988.
Jacques, C. A. J. et al., Br. J. Pharmacol., 95:562-568 (1988).
Lefer, A. M. et al., Proc. Natl. Acad. Sci. USA, 85:8340-8344 (1988).
Badr, K. F. et al., J. Clin. Invest., 81:1702-1709 (1988).
Sheard, P. et al., in The Development of Anti-Asthma Drugs, D. R. Buckle, et al., eds., Butterworth, London, pp. 133-158 (1988).
Lefer, A. M. et al., ISI Atlas Sci. (Pharmacology), 2:109-115 (1988).
Cashman, J. R. et al., Drugs of Today, 24:723-732 (1988).
Badr, K. F. et al., Am. J. Physiol., 22:F239-F243 (1987).
Badr, K. F. et al., Biochm. Biophys. Res. Commun., 145:408-414 (1987).
Badr, K. F. et al., in Advances in Prostaglandin, Thromboxane and Leukotriene Research, vol. 19, B. Samuelsson et al., eds., Raven Press, New York (1989), pp. 233-236.
DeBoer, D. K. et al., Kidney Int. (Proc. 21st Annual Mtg. of the Am. Soc. Nephrology), Dec. 11-14, 1988.
Nicolaou et al., Chem. Abstracts, 1989, vol. 111:76329v.

Primary Examiner—Lester L. Lee
Assistant Examiner—Stephen B. Maebius

[57] ABSTRACT

Composition and methods are disclosed for antagonizing SRS-A, and especially LTD$_4$, comprising the administration of LXA$_4$ or an active derivative thereof to an animal. These compositions and methods are useful in the control of hemostasis, vascular reactivity, and especially vasoconstriction, and anaphylactic and allergic reactions in animals.

22 Claims, 4 Drawing Sheets

USE OF LIPOXIN A₄ AND ITS DERIVATIVES AS ANTAGONISTS FOR SLOW-REACTING SUBSTANCES OF ANAPHYLAXIS

This invention was made with government support; the government has certain rights in this invention.

FIELD OF THE INVENTION

This invention is in the area of vasodilators. Specifically, this invention is directed to medicinal compositions comprising lipoxin $A_4$ ($LXA_4$) or derivatives of this compound and their use as leukotriene $D_4$ ($LTD_4$) receptor antagonists to alleviate leukotriene-mediated vascular constriction. These compositions and methods are useful in the treatment of hemostasis, vascular reactivity and inflammation, and especially anaphylactic and allergic reactions in animals.

BACKGROUND OF THE INVENTION

Lipoxygenase products of arachidonic acid (eicosatetraenoic acid) display a diverse array of biological activities (Samuelsson, B., et al . Science 237:1171–1176 (1987)). At least four major classes of lipoxygenase-derived products of arachidonic acid metabolism have been identified: hydroperoxides (for example, 12-HPETE, 15-HPETE), non-peptidic leukotrienes (for example, $LTB_4$), sulfidopeptide leukotrienes (for example $LTC_4$, $LTD_4$, and $LTE_4$) and lipoxins. Generally, these classes are grouped together as lipoxygenase-derived eicosanoids (LDE); however, each class has a distinct profile of biological activities.

Lipoxins (lipoxygenase interaction products) are a novel series of arachidonic acid derived metabolites which have been characterized only recently (Serhan, C. N. et al., *Biochem. Biophys. Res. Commun.* 18:943–949 (1984); Serhan, C. N. et al., *Proc. Natl. Acad. Sci. USA* 5335–5339 (1984)). The distinguishing feature of the lipoxin chemical structure is the presence of a trihydroxy conjugated tetraene structure. At least two biologically active lipoxins have been characterized; $LXA_4$ ((5S,6R,15S)-5,6,15-trihydroxy-7,9,13-trans-11-cis-eicosatetraenoic acid) and $LXB_4$ ((5S,14R,15S)-5,14,15-trihydroxy-6,10,12-trans-8-cis-eicosatetraenoic acid (Serhan, C. N. et al., *J. Biol. Chem.* 261:16340–16345; Serhan, C. N. et al., *Proc. Natl. Acad. Sci. USA* 83:1983–1987 (1986)).

Very little is known about the biological roles or activities of the lipoxins. It has been suggested to use $LXB_4$ to treat diseases characterized by inflammation mediated through the activation of neutrophils such as that found in asthma, arthritis, physical trauma and radiation exposure (Morris, J., U.S. Pat. No. 4,576,758; Samuelsson, B. et al., U.S. Pat. No. 4,560,514).

$LXA_4$ has been shown to contract pulmonary smooth muscle (guinea pig lung), but not guinea pig ileum or trachea, and to relax (dilate) vascular smooth muscle at concentrations of less than 1 μM (Dahlen, S.-E. et al., Acta Physiol. Scand. 130:643–647 (1987)). Topical administration of $LXA_4$ to the hamster cheek pouch induces a pronounced arteriolar dilation, but does not change venular diameters (Dahlen, S.-E. et al., in *Adv. Exper. Med. Biol.* 229: Chapter 9, pp. 107–130, 1988). $LXA_4$ has also been shown to induce neutrophils to generate superoxide radicals, release elastase, and promote chemotaxis by leukocytes (Serhan, C. N. et al., in *Prostaglandins, Leukotrienes and Liooxins*, J. M. Bailey, ed., Plenum, N.Y., pp. 3–16, 1985).

It has been suggested to use $LXA_4$ to induce the inflammatory response of neutrophils so as to provide an experimental model to evaluate the efficacy of compounds such as $LXB_4$ derivatives in preventing this response (Samuelsson, B. et al., U.S. Pat. No. 4,560,514). It has also been suggested that $LXA_4$ may exert some of its biological effects by binding to the $LTD_4$ receptor (Jacques, C. A. J. et al., *Br. J. Pharmacol.* 95: 562–568 (1988)) and that $LXA_4$ and $LTD_4$ may even share a common receptor (Lefer, A. M. et al., *Proc. Natl. Acad. Sci. USA* 85:8340–8344 (1988)).

Slow-reacting substances of anaphylaxis (SRS-A) are considered to be the physiological mediators of anaphylactic and allergic reactions in animals. SRS-A consist primarily of a mixture of the LDE leukotrienes $LTC_4$ and $LTD_4$.

The release of SRS-A has also been implicated as the underlying cause of disorders of the mucociliary and cardiovascular system. SRS-A induced contraction of bronchial smooth muscle results in impairment of ventilatory function in allergic asthma. SRS-A induced impairment of mucus clearance leads to mucus plugging of the airways and bronchial hyper-reactivity seen in subjects with asthma. SRS-A induced pulmonary hypertension plays a role in cor polmonale, chronic bronchitis and emphysema. SRS-A induced negative inotropism, coronary vasoconstriction and increased vascular permeability have an effect on the cardiovascular system. SRS-A also participates in mediating the functional consequences of glomerular inflammatory injury (Badr, K.F., et al., *J. Clin. Invest.* 81:1702–1709 (1988)).

Inhibition of SRS-A, and amelioration of the physiological consequences of SRS-A, can occur either by blocking release of SRS-A or by blocking the actions of released SRS-A. Thus inhibition of the actions of SRS-A may be used to alleviate and treat the above disorders.

It is known to inhibit physiological responses to SRS-A by blocking the $LTD_4$ receptor with $LTD_4$ receptor antagonists. Sheard et al. have described a synthetic compound, FPL 55712, and derivatives thereof, which inhibit the SRS-A response by acting as $LTD_4$ receptor antagonists (Sheard, P. et al., in *The Develooment of Anti-Asthma Drugs*, D. R. Buckle et al., eds., Butterworth, London, 1984, pp.133–158). However, FPL-55712 is short-acting. Other antagonists of SRS-A have been reported (for example, Gleason, J. G. et al., *J. Med. Chem.* 30:959–961 (1987)) including many which retain close structural similarity with FPL 55712 (Fleisch, J. H., et al., *J. Pharmacol. Exp. Ther.* 233:148 (1985); Young, R. N. et al., *J. Med. Chem.* 29:1573 (1986); O'Donnell, M. et al., *Ann. Allergy* 278 (1985). However, most of these compounds exhibit a low affinity for $LTD_4$ receptors, are orally inactive or exhibit low bioavailability. The status of currently known $LTD_4$ receptor antagonists has been recently reviewed (Lefer, A. M., *ISI Atlas Sci. (Pharmacology)* 2:109–115 (1988); Cashman, J. R. et al., *Drugs of Today* 24:723–732 (1988); Fleisch, J. H. et al., *Ann. N. Y. Acad. Sci.* 524:356–368 (1988); Musser, J. H. et al., *Agents and Actions* 18:332–341 (1986)).

Studies in human neutrophils, have established an inverse relation between the generation of lipoxins and leukotrienes following exposure of these cells to 15-HETE and the calcium ionophore A23187 (Serhan, C. N., in *Advances in Prostaglandin, Thromboxane and Leukotriene Research*, Samuelsson, B., et al. (eds.), Raven Press, N.Y., Volume 18). In addition, recent results indicate that mesangial cells can generate lipoxins from exogenous sources of $LTA_4$ (Garrick, R., et al., *Kidney Int. Proceedings* 21st Annual Meeting of the American Society of Nephrology, Vol. 25, p. 292 (1989)), which may be provided by activated leukocytes (e.g., during transcellular metabolism). Thus, the local levels of these compounds may be elevated following the infiltration of leukocytes into the glomerulus.

Use of $LTD_4$ receptor antagonists which are based on a natural product would be preferable to the use of completely synthetic compounds in that the natural products would ameliorate the physiological consequences of leukotriene-induced physiological injury with greater bioavailability and less toxicity than the synthetic inhibitors. Thus it is desirable to develop SRS-A antagonists which are natural compounds or derivatives thereof.

SUMMARY OF THE INVENTION

In response to the long-standing need for controlling the vasoconstriction associated with SRS-A, the present invention was developed. Recognizing that current compounds used as antagonists of the $LTD_4$ receptor were derived from a chemical structure unrelated to a natural product, the inventors postulated that fewer side effects and better bioavailability might be obtained with a natural antagonist of SRS-A or a compound structurally derived from a natural antagonist. The present invention is directed to compositions comprising natural antagonists of SRS-A, and especially of $LTD_4$. Further, the invention is directed to methods for antagonizing SRS-A, and especially $LTD_4$, in an animal, such methods comprising administration of antagonist-effective amounts of $LXA_4$ or an active derivative thereof to such animal. These antagonists and methods are useful in the treatment of physiological disorders in which $LTD_4$ receptors play a contributing role, for example, hemostasis, vascular reactivity, and especially vasoconstriction, inflammation, and anaphylactic and allergic reactions.

Definitions

Figure 1:
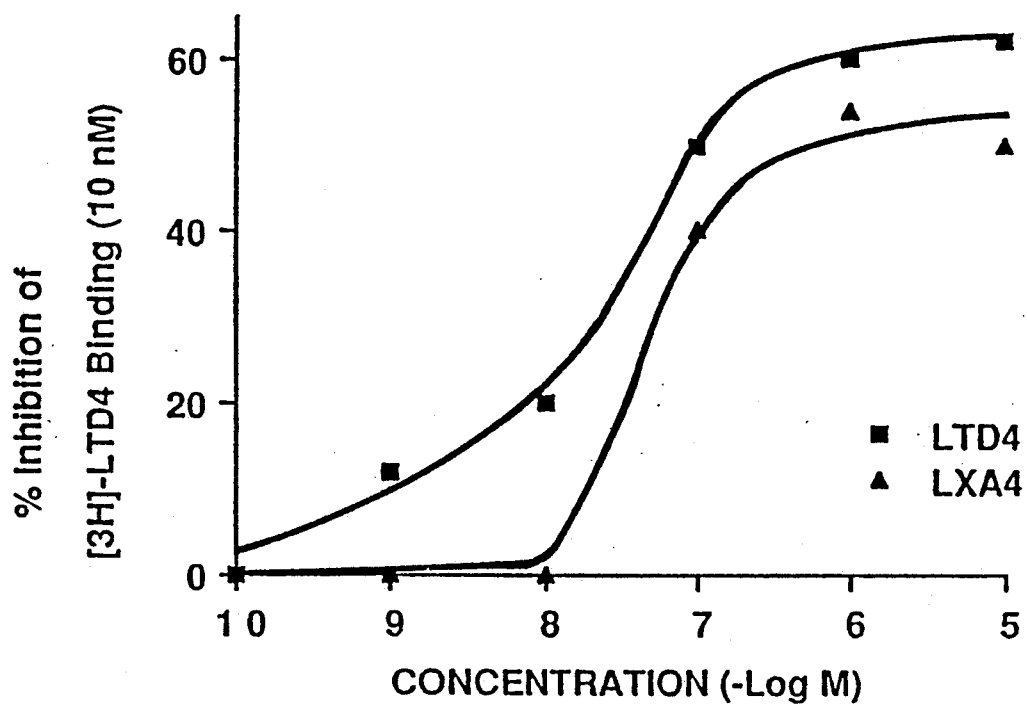
FIG. 1 is a plot of the percent inhibition of $[^3H]LTD_4$ (10 nM) binding to rat glomerular mesangial cells by $LTD_4$ (squares) and $LXA_4$ (triangles). Each point represents the mean of four experiments performed in duplicate.

In order to provide a clearer and consistent understanding of the specification and claims, including the scope to be given such terms, the following definitions are provided.

$LXA_4$. By "$LXA_4$" is meant lipoxin $A_4$ or an active derivative thereof, including synthetic analogues of $LXA_4$ which are converted by the body of $LXA_4$ or an active derivative thereof, and pharmaceutically suitable salts thereof.

Pharmaceutically Acceptable Salts. By the term "pharmaceutically acceptable salts" is intended salts formed from pharmaceutically acceptable acids or bases, e.g., acids such as sulfuric, hydrochloric, nitric, phosphoric acid, etc. or bases such as alkali or alkaline earth metal hydroxides, ammonium hydroxides, alkyl ammonium hydroxides, etc.

Animal. By the term "animal" is intended all animals in which $LXA_4$ is capable of antagonizing $LTD_4$ receptor responses. Foremost among such animals are humans; however, the invention is not intended to be so limiting, it being within the contemplation of the present invention to treat any and all animals which may experience the beneficial effects of the invention.

Receptor. The term "receptor" is intended to refer generally to a functional macromolecule or complex of macromolecules with which certain groups of cellular messengers, such as LDE's, hormones and neurotransmitters, must first interact before the biochemical and physiological responses to those messengers are initiated. Therefore, as used herein, the term "receptor" is used operationally to denote any cellular macromolecule (or complex of macromolecules) to which a chemical or macromolecular entity specifically binds to initiate its effects.

Agonist. The term "agonist" is intended to refer generally to a chemical agent which mimics at least some of the effects of a natural chemical messenger by interaction with the appropriate physiological receptor for the natural messenger.

Antagonist. The term "antagonist" is intended to refer generally to a chemical compound which is able to bind to the receptor for a natural chemical messenger, but which has no intrinsic physiological activity at that receptor and does not invoke the physiological response mediated by activation of that receptor. As recognized by those skilled in the art, the binding of an antagonist results in an interference with the effect of the natural ligand or with an agonist. As used herein, compounds that are themselves devoid of intrinsic pharmacological activity but cause effects by inhibition of the action of a specific messenger, by competition for receptor binding sites, are designated as antagonists. Thus, a method for "antagonizing" a response to specific agents such as SRS-A is a method in which the natural binding of SRS-A to specific SRS-A receptors is interferred with so as to block the activation of such receptors.

Response. The term "response" is intended to refer to a change in any parameter which can be used to measure and describe an effect associated with interaction of a chemical agent with the $LTD_4$ receptor. The response may be a physical one such as a change in the vascular reactivity, renal glomerular dynamics or pulmonary functioning; or, it may be a molecular one for example, a change in a level of a metabolite, (for example, $IP_3$) or protein, receptor, enzyme, or genomic expression.

Controlling. By "controlling" a response, for example, controlling vasoconstriction, is mean ameliorating, reversing, regulating or interfering with such response, wherein such amelioration, reversal, regulation or interference is the result of administration of anti-response effective amounts of a desired agent. Thus, administration of anti-vasoconstrictive effective amounts of an anti-vasoconstriction agent results in amelioration, reversal, regulation or interference with vasoconstriction. Such administration may be used to medically "treat" the response in an animal so as to improve a medical disorder, disease or symptom associated with the response.

Agent. The term "agent," for example a anti-vasoconstriction agent, is intended to refer generically to any compound which interacts with the stated receptor or response.

DETAILED DESCRIPTION OF THE INVENTION

The present invention comprises methods of treating leukotriene-induced vasoconstriction by administration of efficacious levels of $LXA_4$ and derivatives thereof. The compounds of the invention are $LTD_4$ receptor antagonists and inhibit $LTD_4$ receptor action; this makes the compounds useful in the treatment and prevention of disorders and disease states wherein leukotriene-induced vasoconstriction is implicated as a contributing or causative agent such as, but not limited to, disorders resulting from the release of SRS-A, and especially asthma, anaphylactic reactions, allergic reactions, shock, circulatory disease states and inflammatory reactions such as, for example, rheumatoid arthritis, gout, psoriasis, allergic rhinitis, adult respiratory distress syndrome, Crohn's disease, endotoxin shock, traumatic shock, hemorrhagic shock, bowel ischemic shock (i.e. splanchnic artery occlusion shock), renal glomerular disease, benign prostatic hypertrophy, inflammatory bowel disease, and/or myocardial ischemia and infarction, circulatory shock, brain injury, systemic lupus erythematlosus, and hypertension, especially essential hypertension and malignant hypertension.

The methods of the invention are based on the inventors' discovery that selective administration of $LXA_4$ into the renal artery of anesthetized rats elicits vasodilator responses in renal arterioles, and reduces the flomerular capillary ultrafiltration coeffcicient ($K_f$) (Badr, K. F. et. al., *Am. J. Physiol.* 22:F239–F243(1987); badr, K. F., et al., *Biochem. Biophys. Res. Comm.* 145:408–414 (1987)). The latter results from the concerted contractile action of smooth muscle-containing glomerular mesangial cells which reduces the glomerular capillary area available for ultrafiltration and, hence, $K_f$. Since the orientation of the plar groups is similar in the peptido-Lts and $LXA_4$ (i.e., 5S,6R) and is a crucial requirement for biologic activity of these eicosanoids, the inventors investigaged whether $LXA_4$-induced falls in $K_f$ were due, in part, to interaction with the mesangial cell $LTD_4$ receptor. Surprisingly, the inventors discovered that $LXA_4$ was capable of binding to the mesangial cell $LTD_4$ receptor and of acting as a $LTD_4$ receptor antagonist. The inventors realized that $LXA_4$ would function as a $LTD_4$ receptor antagonist in any tissue sensitive to $LTD_4$ action. Such a finding is a significant advance in the treatment of the functional consequences of glomerular inflammatory reactions (Badr, K. F., et al. *J. Clin. Invest.* 81:1702–1709 (1988); Badr, K. F., in *Advances in Prostaglandin, Thromboxane and Leukotriene Research*, Samuelsson, B., et al. (eds.), Raven Press, N.Y., Volume 18 (1989); and Badr, K. R. et al., *Proc. Natl. Acad. Sci. USA* 86:(1989), incorporated herein by reference)).

$LXA_4$ can be isolated from leukocytes exposed to 15-HPETE ((15S), 15-hydroperoxy-5,8,11-cis-13-trans-iecosatetraenoic acid (Serhan, C. N. et al., *J. Biol. Chem.* 261:16340–16345 (1986)), incorporated herein by reference, or chemically synthesized (Webber, S. E. et. al., *Adv. Exper. Med. Biol.* 229:61–78 in *Lipoxins: Biosynthesis, Chemistry, and Biological Activities*, P. Wong et al., eds., Plenum Publishing Corporation, New York, 1988).

As will be understood by one of skill in the art, derivatives of $LXA_4$ may be constructed which, while retaining the ability of the natural compound to act as a $LTD_4$ receptor antagonist, have an enhanced bioavailability, half-life, affinity for the $LTD_4$ receptor, or other desirable property. Such derivatives may include covalent substitutions at one or more of the three hydroxyl groups and/or at the terminal carboxyl group of $LXA_4$. Especially, such substitutents include esterification of the carboxyl group, and preferably, the α-methyl ester derivative thereof. Substitutents at carbon positions 5, 6, and 15 include addition of the acetate, methyl, of n-butylboronate derivative.

$LXA_4$ and derivatives thereof can be administered by any method which results in deliverance of efficacious levels of said $LXA_4$ or derivatives thereof such that amelioration of the targeted leukotriene-based physiological disorder occurs. For example, $LXA_4$ may be administered parenterally, orally, or topically, in dosage unit formulations containing conventional nontoxic pharmaceutically acceptable carriers, adjuvants and vehicles as desired. The term parenteral as used herein includes subcutaneous, intravenous, intraarterial injection or infusion techniques, without limitation. The term "topically" encompasses administration rectally and by inhalation spray (aerosol), as well as by the more common routes of the skin and the mucous membrane of the mouth and nose.

Total daily doses of the compounds of this invention administered to a host in single or divided doses may be in amounts, for example, of from about 0.1 to about 10 mg/kg body weight daily and more preferrably 0.5 to 5 mg/kg/day. Dosage unit composition may contain such amounts of such submultiples thereof as may be used to make up the daily doses. It will be understood however, that the specific dose level for any particular patient will depend upon a variety of factors including the body weight, general health, sex, diet, time and routine of administration, rates of absorption and excretion, combination with other drugs and the severity of the particular disease being treated.

This invention also provides for compositions in unit dosage form for the suppression or inhibition of $LTD_4$ receptor activity in a human or lower animal host in need of such treatment, comprising $LXA_4$ or an active derivative thereof and one or more nontoxic pharmaceutically acceptable carriers, adjuvants, or vehicles. The amount of active ingredients that may be combined with such materials to produce a single dosage form will vary depending upon various factors, as indicated above. As described herein, variety of materials can be used as carriers, adjuvants and vehicles in the composition of this invention, as available in the pharmaceutical arts.

Injectable preparations, such as oleaginous solutions, suspensions or emulsions, may be formulated according to known art, using suitable dispersing or wetting agents and suspending agents, as needed. When the active compounds are in water-soluble form, for example, in the form of water soluble salts, the sterile injectable preparation may employ a nontoxic parenterally acceptable diluent or solvent as, for example, sterile nonpyrogenic water or 1,3-butanediol. Among the other acceptable vehicles and solvents that may be employed are 5% dextrose injection, Ringer's injection and isotonic sodium chloride injection (as described in the USP/NF). When the active compounds are in a non-water soluble form, sterile, appropriate oily suspensions containing suitable lipophilic solvents or vehicles, such as fatty oil, for example, sesame oil, or synthetic fatty acid esters, for example, ethyl oleate or triglycerides, are used. Alternatively, aqueous injection suspensions which contain substances which increase the viscosity, for example, sodium carboxymethyl cellulose, sorbitol, and/or dextran, and optionally also contain stabilizers may be used.

The pharmaceutical preparations of the present invention are manufactured in a manner which is in itself know, for example, by means of conventional mixing, granulating, dragee-making, dissolving, or lyophilizing processes. Thus, pharmaceutical preparations for oral use can be obtained by combining the active compounds with solid excipients, optionally granulating a resulting mixture and processing the mixture or granules, after adding suitable auxiliaries, if desired or necessary, to give tablets of dragee cores.

Suitable excipients are, in particular, fillers such as sugars, for example lactose or sucrose, mannitol or sorbitol, cellulose preparations and/or calcium phosphates, for example tricalcium phosphate or calcium hydrogen phosphate, as well as binders, such as starch, pastes, using, for example, maize starch, wheat starch, rice starch, or potato starch, gelatine, tragacanth, methyl cellulose, hydroxypropylmethyl cellulose, sodium carboxymethyl cellulose, and/or polyvinyl pyrrolidone, and/or, if desired, disintegrating agents, such as the above-mentioned starches, and also carboxymethylstarch, cross-linked polyvinyl pyrrolidone, agar or alginic acid or a salt thereof, such as sodium alginate. Auxiliaries are, above all, flow-regulating agents and lubricants, for example, silica, talc, stearic acid or salts thereof, such as magnesium stearate or calcium stearate, with suitable coating, which if desired, are resistant to gastric juices and for this purpose, inter alia concentrated sugar solutions, which optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetyl cellulose phthalate or hydroxypropylmethyl cellulose phthalate, are used. Dyestuffs or pigments may be added to the tablets or dragee coatings, for example, for identification or in order to characterize different combinations of active compound doses.

Other pharmaceutical preparations which can be used orally are push-fit capsules made of gelatin, as well as soft, sealed capsules made of gelatin and a plasticizer such as glycerol or sorbitol. The push-fit capsules can contain the active compounds in the form of granules, for example, mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin or liquid polyethylene glycols, it also being possible to add stabilizers.

Suppositories for rectal administration of the compound of this invention can be prepared by mixing the drug with suitable suppository bases such as a nonirritating excipient, for example, cocoa butter, natural or synthetic triglycerides, paraffin hydrocarbons, polyethylene glycols, or higher alkanols, and especially bases which are solid at ordinary temperature but liquid at body temperature and which therefore melt in the rectum and release the drug. In addition, it is possible to use gelatin rectal capsules which consist of a combination of the active compounds with a base; possible base materials are, for example, liquid triglycerides, polyethylene glycols, or paraffin hydrocarbons.

Solid dosage forms for oral administration include capsules, tablets, pills, troches, lozenges, powders and granules. In such solid dosage forms, the active compound may be admixed with at least one inert diluent such as sucrose, lactose or starch. Such dosage forms may also comprise, as is normal practice, pharmaceutical adjuvant substances, e.g., stearate lubricating agents. Solid oral preparations can also be prepared with enteric or other coatings which modulate release of the active ingredients.

Liquid dosage forms for oral administration include pharmaceutically acceptable emulsions, solutions, suspensions, syrups and elixirs containing inert nontoxic diluents commonly used in the art, such as water and alcohol. Such compositions may also comprise adjuvants, such as wetting agents, emulsifying, suspending, sweetening, flavoring and perfuming agents.

The compositions of the present invention, in and of themselves, find utility in the control of vasoconstriction, be it chronic or acute. The compositions for the present invention direct the body's own mechanisms for dealing with vasoconstriction to its maximum potential. In intravenous dosage form, the compositions of the present invention have a sufficiently rapid onset of action to be useful in the management of vasoconstriction of short duration such as that found in vasospastic responses or malignant hypertension.

Additionally, a low potency version is useful in the management of mild or chronic vasoconstriction. This low potency version is useful in the management of essential hypertension, and chronic renal disease.

Further, it has also been found that the compositions of the present invention are useful in the management of chronic severe vasoconstriction such that associated with cardiovascular disease and glomerular kidney disease.

In addition, the compounds of the present invention provides insight into the structural requirements for leukotriene receptor activation and show that lipoxins can serve as structural models for the design of more potent receptor level antagonists for the peptidoleukotrienes.

The following examples are illustrative, but not limitative of the method and composition of the present invention. Other suitable modifications and adaptations of the variety of conditions and parameters normally encountered in clinical therapy and which are obvious to those skilled in the art are within the spirit and scope of this invention.

EXAMPLES

Statistical: ANOVA with Bonferroni modification for multiple pre-planned comparisons was used, within each group and between groups, to compare the changes in various whole kidney and microcirculatory indices which occurred from one period to another. In phosphoinositide generation studies, increases in [$^3$H]-IP$_3$ CPMs in agonist-treated cells were compared to vehicle-treated controls using upaired students t-test.

Differences were considered significant at a p value ≦0.05. All values are reported as means ± SEM.

EXAMPLE 1

Binding of $LXA_4$ to $LXA_4$ Receptors In Kidney Mesangial Cells

The ability of $LXA_4$ to bind to sesangial cell $LTD_4$ receptors in a concentration-dependent manner was investigated in mesangial cell cultures.

Mesangial Cell Culture: Rat mesangial cells were isolated and cultured as described previously (Harris, R. C., et al., *J. Clin. Invest.* 82:1028-1039 (1988). Briefly, kidneys were exicesed from two young Sprague-Dawly rats under sterile conditions, and the cortices removed, minced, and washed several times in Hank's Balanced Salt Solution, containing 10 mM HEPES pH 7.4, amphotericin (0.25 µg/ml), and gentamicin (50 µg/ml). The tissue was then passed through consecutive sterilized stainless mesh filters with pore sizes of 212 µm, 150 µm, and then onto the final mesh of 75 µm. The isolated glomeruli were harvested from the surface of the 75 µm. The isolated glomeruli were harvested from the surface of the 75 µm filter and washed twisce with the Hank's Media. The glomeruli were suspended in RPMI 1640 Medium with 15% Fetal Bovine Serum (Givco), penicillin (100 µ/ml) and streptomycin (100 µg/ml) (Gibco), plated into 100 mm cell culture petri dishes, and incubated at 37° C. in a humidified atmosphere of 95% air and 5% air and 5% $CO_2$. Mesangial cell colonies were subcultured in 60 mm culture dishes, and experiments were carried out in cells from passages 2 to 12. The criteria used to establish the identify of mesangial cells were as described previously (Harris, R. C., et al., *J. Clin. Invest.* 82:1028-1039 (1988)). Cells were routinely grown in RPMI-1640, supplemented with 20% fetal calf serum, penicillin 100 µ/ml, and streptomycin 100 µg/ml. $[^3H]$-$LTD_4$ Binding Studies: $LXA_4$ was obtained from Biomol Research Laboratories Inc., Philadelphia, Penna. and $[14,15-^3H]$ $LTD_4$ (32.0 Ci/mmol) was obtained from New England Nuclear. All eicosanoids were stored under argon at −70° C. in methanol and their purity and quantity verified periodically by ultraviolet scanning and high pressure liquid chromatography (Serhan, C. N. et al., *J. Biol. Chem.* 261:16340 (1986)).

Studies of $[^3H]$-$LTD_4$ binding were performed on mesangial cells grown to confluence in 24-well cluster dishes. Preliminary experiments indicated that increased [3H]-$LTD_4$ binding in other systems (Lewis, M. A., et al., *Biochem. Pharmacol.* 34:4311-4317 (1985); Sarau, H. M., et al., *J. Biol. Chem.* 262:4034-4041 (1987)). Therefore, experiments were performed in a buffer previously determined to optimize $[^3H]$-$LTD_4$ binding (Sarau, H. M., et al., *J. Biol. Chem.* 262:4034-4041 (1987); Mong, S., et al., *Mol. Pharmacol.* 32:223-229 (1987)) consisting of 20 mM HEPES, 10 mM $CaCl_2$, 10 mM $MgCl_2$, 5 mM glycine and 5 mM cysteine (Buffer A). Binding studies were routinely performed at 4° C. Cells were washed once with buffer A and then exposed to the appropriate concentration of $[^3H]$-$LTD_4$ in buffer A. At the completion of the experiment, the experimental medium was removed and the cells were washed 5 times with ice-cold buffer. The cells were then dissolved with 1.0 ml of 1.0 N NaOH, neutralized with HCl, dissolved in 10 ml of Aquasol (New England Nuclear, Boston, MA), and the bound radioactivity was determined using a scintillation counter (Beckman Instruments). Non-specific binding was determined by measuring the amount of $[^3H]$-$LTD_4$ bound in the presence of 1000-fold excess of unlabeled $LTD_4$. Cell density was determined by counting cells from replicate wells, using a Coulter Counter ZBi (Coulter Electronics, Inc., Hialeah, Fla.).

Competitive binding-inhibition studies were carried out by incubation of mesangial cells with 10 nM $[^3H]$-$LTD_4$ and addition, at equilibrium, of 10-fold to 1000-fold increasing concentrations of $LXA_4$.

FIG. 1 depicts the percent inhibition of the binding of 10 nm $[^3H]$-$LTD_4$ by $LTD_4$ and $LXA_4$ In early passage cultured mesangial cells, $LXA_4$ was a potent competitor for $[^3H]$-$LTD_4$ binding in a manner similar to that of unlabeled $LTD_4$ (FIG. 1). Half maximal inhibition of binding by $LXA_4$ was at 100 nM compared to 100 nM for the homoligand.

Competition by $LXA_4$ was equipotent to that of $LTE_4$ and several-fold greater than that of the non-peptidoleukotriene, $LTB_4$. The potent $[^3H]$-$LTD_4$ binding inhibition obtained with $LXA_4$, compared to the relatively weak competitive properties of the biologically inactive 5R,6S-$LTD_4$ isomer, suggests strongly that the S,R orientation of the polar substituents at C5 and C6 confers optimal advantage for receptor recognition and biological activity. This is supported by additional studies in which 6S-$LXA_4$ (5S,6S,15S,trihydroxy-7,9,13-trans-11-cis-eicosatetraenoic acid) filed to compete for $[^3H]$-$LTD_4$ even at a 1000-fold excess concentration.

These results demonstrate that the binding of $[^3H]$-$LTD_4$ to rat mesangial cells displays a number of characteristics which suggest the presence of specific, membrane-bound receptors for this eicosanoid on mesangial cells. The presence of such receptors takes on particular importance in view of the demonstrated functional responses of mesangial cells to exogenous $LTD_4$ and their possible relevance during inflammatory glomerular injury: $LTD_4$ contracts mesangial cells in culture (Barnett, R., et al., *Am. J. Physiol.* 19:F838-F844 (1986); Simonson, M. S., et al., *Kidney Int.* 30:524-531 (1986)), markedly reduces $K_f$ and GFR in vivo (Badr, K. F., et al., *Am. J. Physiol.* 22:F239-F243 (1987); Badr, K. F., et al., *Circ. Res.* 54:492-499 (1984)), and, through these actions, plays an important role in mediating the impairment of glomerular filtration and permselectivity functions in experimental models of glomerulonephritis (Badr, K. F., et al., *J. Clin. Invest.* 81:1702-1709 (1988)).

EXAMPLE 2

Figure 2:
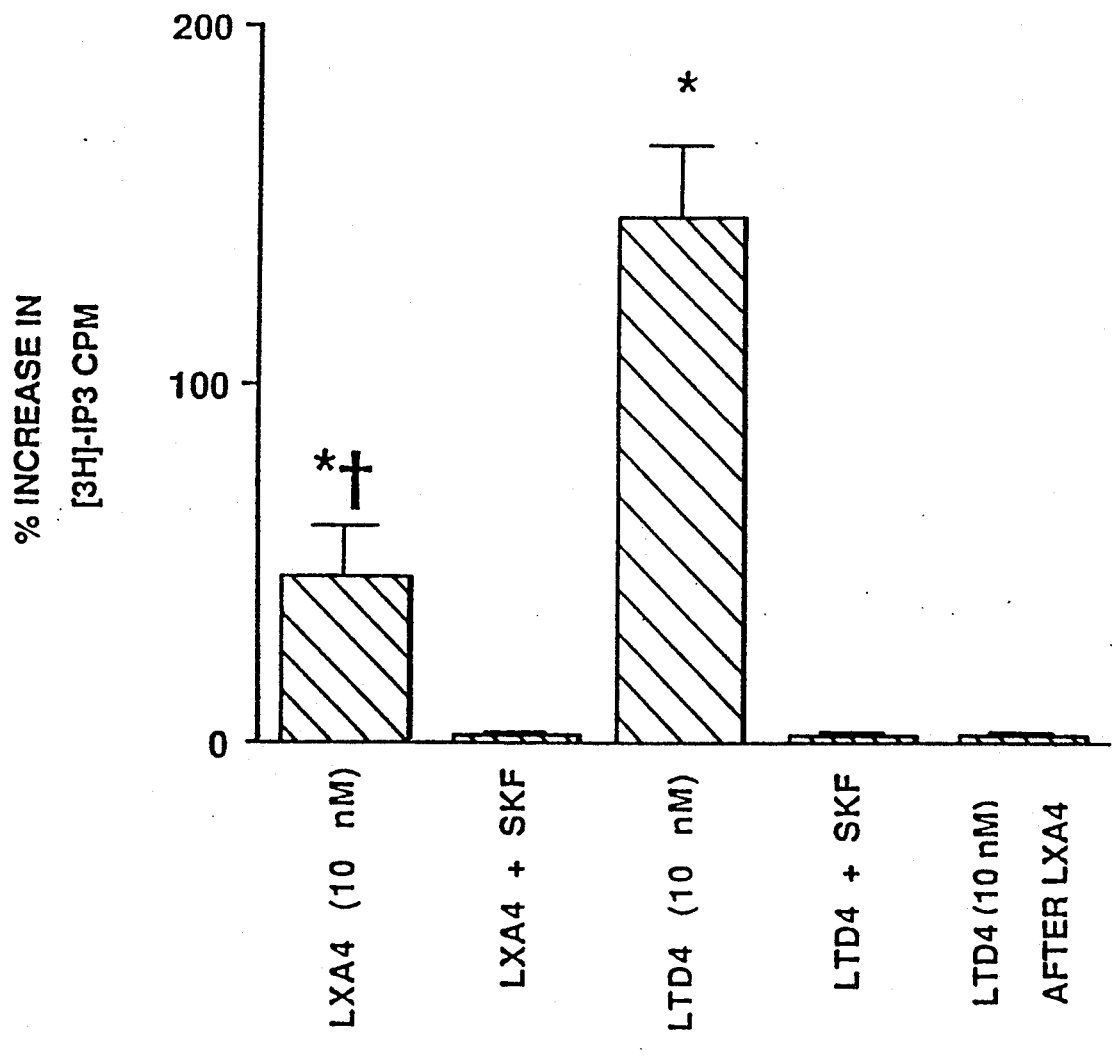
FIG. 2 is a plot of inositol triphosphate ($IP_3$) formation in rat mesangial cells in response to $LXA_4$ and $LTD_4$ and its complete abolition in the presence of 100-fold concentrations of SKF 104353 (SKF). The far-right column depicts the abrogation of $LTD_4$-induced stimulation of $IP_3$ formation by preexposure of the cells to 100 nM $LXA_4$ for 10 minutes. *, $P<0.01$ versus vehicle-stimulated controls. +, $P,0.05$ versus $LTD_4$ alone.

Inhibition of $LTD_4$-Induced $IP_3$ Formation by $LXA_4$ $LXA_4$ also blocked $LTD_4$-induced stimulation of $IP_3$ formation (FIG. 2). To label mesangial cells with $[^3H]$-Inositol, cells grown to confluence in 60 mm culture dishes ($10^6$ cells/dish) were cultured in RPMI, supplemented with 10% dialyzed fetal calf serum and $[^3H]$-inositol (1 µCi/ml) in a total incubation volume of 5 ml. Preliminary experiments revealed that incorporation of label was maximal at 48 hours and stable for up to 72 hours. All subsequent experiments were therefore carried out on cells preincubated with $[^3H$-inositol for 48-60 hours.

The formation of inositol monophosphate (IP6hd 1), inositol bisphosphate ($IP_2$), and $IP_3$ in $[^3H]$-inositol labeled mesangial cells in response to either $LTD_4$ or $LXA_4$ was measured as follows: plates were washed with Krebs-Ringer Solution contaiing 118 mM NaCl, 4.6 mM KCl, 24.9 mM NaHCO$_3$, 1 mM KH$_2$PO$_4$, 11.1 mM glucose, 1.1 mM MgSO$_4$, 1.0 mM CaCl, 5 mM HEPES, and 0.1% BSA, pH 7.4, 37° C. Increasing concentrations (0.1 to 100 nM) of LTD$_4$, LXA$_4$, or LTD$_4$ following preincubation of cells with 100-fold concentration LXA$_4$ for 10 min were then added to 2 ml of warmed (37° C.) Krebs-Ringer and the cells incubated for the indicated time. In experiments in which the effect of the LTD$_4$ antagonist, SKF 104353, on IP formation was tested, the cells were preincuated in the presence of this agent for 10 min prior to addition of agonist (Mong, S., et al., *Mol. Pharmacol.* 32:223-229 (1987); Gleason, J. G., et al., *J. Med. Chem.* 30:959-961 (1987)). Reactions were terminated by the addition of cold 10% trichloroacetic acid (TCA), the supernatants subjected to ether extraction, and the aqueous phase titrated to neutral pH using 0.1 M Tris base. [$^3$H]-IP$_1$, [$^3$H]-IP$_2$, and [$^3$H]-IP$_3$ in the aqueous phase were separated and quantitated by anion exchange column chromatography, using the method of Berridge et al. (Berridge, M. J., *Biochem. J.* 220:345-360 (1984)). To ensure the reliability of the separation technique, the same methods for extraction and separation were applied to known amounts of [$^3$H]-IP$_1$, [$^3$H]IP$_2$, and [$^3$H]-IP$_3$ standards (New England Nuclear) mixed in a ratio of 3:2:1, respectively, and subjected to separation by HPLC. The latter was performed using established methodology described previously (Cunha-Melo, J. R., et al., *J. Biol. Chem.* 262:11455-11463 (1987)). The results from both separation techniques revealed indistinguishable differences in the percentage of recovered counts (about 80%) and the quantitative ratio of the three IPs separated.

Phosphoinositide hydrolysis in mesangial cells was measured five secs after addition of 1 nM (n=3), 10 nM (n=6), 50 nM (n =3), and 100 nM (n=5) LXA$_4$ to mesangial cells labeled with [$^3$H]-inositol. Low but significant increases [46±14% (p<0.05), 50±21% (p<0.05), 44±22% (p<0.05), and 45±26% (p<0.05), respectively] in radioactive counts (CPM) corresponding to IP$_3$ formation by these cells was noted over those obtained in vehicle-treated samples (controls). Addition of 10 nM (n=5) and 50 nM (n=4) LTD$_4$ to these cells was associated with 146±20% (p<0.01) and 106±13% (p<0.005) increases in [$^3$H]-IP$_3$ counts as compared to controls, values significantly greater than those for LXA$_4$ (p<0.05). Incubation of the mesangial cells with the LT04 receptor antagonist, SKF 104353, in concentrations 100-fold in excess of the ligand, followed by addition of LTD$_4$ in the 10 and 50 nM concentrations (n=3 for each) was associated with total abrogation of the LTD$_4$-induced stimulation of [$^3$H]-IP$_3$ formation in these cells. Similarly, pre-incubation of these cells with 100 nM LXA$_4$ for 10 min prior to addition of 10 nM LTD$_4$ (n=3) completely prevented LTD$_4$-induced IP$_3$ generation. Incubation of mesangial cells with SKF 104353 (100 nM) also abrogated the stimulation of IP$_3$ formation induced by LXA$_4$ (n=3) (FIG. 2).

Intracellular generation of IP$_3$ is, in general, held to play an important role in mediating responses to various vasoactive agents. The demonstration of a rapid (5 sec) formation of IP$_3$ following addition of LTD$_4$ to mesangial cells is in agreement with reports by other investigators regarding the involvement of phosphoinositide hydrolysis in the signaling of LTD$_4$-mediated biological responses in rat basophilic leukemia cells (Sarau, H. M., et al., *J. Biol. Chem.* 262:4034-4041 (1987)), sheep tracheal smooth muscle cells (Mong, S., et al., *J. Pharmacol. Exp. Ther.* 244: 508-515 (1988)), bovine endothelial cells (Clark, M. A., et al., *Proc. Natl. Acad. Sci. USA* 83:7320-7324 (1986)), and guinea pig lung (Mong, S., et al., *Mol. Pharmacol,* 31:35-41 (1987)). It is reasonable to assume that the contraction of mesangial cells by LTD$_4$ may proceed via a similar mechanism involving the formation of IP$_3$ and mobilization of intracellular Ca$^{2+}$. In fact, the capacity of LTD$_4$ to increase intracellular Ca$^{2+}$ concentrations has been demonstrated recently by Baud et al. in DMSO-differentiated HL-60 myeloid cells (Baud, L., et al., *J. Clin. Invest.* 80:983-991 (1987)). In the present studies, LXA$_4$ elicited similar, though significantly less potent stimulation of IP$_3$ generation in mesangial cells, presumably due to occupancy of the LTD$_4$ receptor. That LXA$_4$-induced IP$_3$ formation is indeed a consequence of LTD$_4$ receptor activation is supported by its total abrogation in the presence of a specific LTD$_4$ receptor antagonist, SKF 104353 (FIG. 2). SKF 104353 is a structural analog of LTD$_4$ and LTE$_4$ that itself is devoid of agonist activity both in vivo (Badr, K. F., et al., *Am. J. Physiol.* 22:F239-F243 (1987); Mong, S., et al., *Mol. Pharmacol.* 32:223-229 (1987)) and in vitro (Mong, S., et al., *Mol. Pharmacol.* 223-229 (1987); Gleason, J. G., et al., *J. Med. Chem.* 30:959-961 (1987)), and it competes for the binding of homoligands to LTD$_4$/LTE$_4$ receptors in a highly potent and specific manner (Gleason, J. G., et al., *J. Med. Chem.* 30:959-961 (1987)), 400- to 500-fold more effectively than the putative leukotriene antagonist, FPL 55712 (Gleason, J. G., et al., *J. Med. Chem.* 30:959-961 (1987)). It is capable of antagonizing and reversing LTD$_4$ effects in a number of tissues, including human and guinea pig lung (Mong, S., et al., *Mol. Pharmacol.* 223-229 (1987)), rat basophilic leukemia cells (Sarau, H. M., et al., *J. Biol. Chem.* 262:4034-4041 (1987)), and renal vasculature (Badr, K. F., et al., *J. Clin. Invest.* 81:1702-1709 (1988)). In systems where it has been tested, SKF 104353 was found to compete specifically with [$^3$H]-LTD$_4$ for binding to whole cells (Sarau, H. M., et al., *J. Biol. Chem.* 262:4034-4041 (1987); Mong, S., et al., *Mol. Pharmacol.* 32:223-229 (1987); Gleason, J. G., et al., *J. Med. Chem* 30:959-961 (1987)), as well as cell membrane fractions (Sarau, H. M., et al., *J. Biol. Chem.* 262:4034-4041 (1987); Mong, S., et al., *Mol. Pharmacol.* 32:223-229 (1987); Gleason, J. G., et al., *J. Med. Chem* 30:959-961 (1987)), and it shifts the dose-response curves obtained for LTD$_4$-mediated phosphoinositide hydrolysis, intracellular calcium mobilization, and thromboxane synthesis (Sarau, H. M., et al., *J. Biol. Chem.* 262:4034-4041 (1987); Mong, S., et al., *Mol. Pharmacol.* 223-229 (1987); Gleason, J. G., et al., *J. Med. Chem* 30:959-961 (1987)). In other studies, we demonstrated the capacity of this antagonist to inhibit [$^3$H]-LTD$_4$ binding to its mesangial cell binding site in a manner similar to that reported for this compound in other systems (Sarau, H. M., et al., *J. Biol. Chem.* 262:4034-4041 (1987); Mong, S., et al., *Mol. Pharmacol.* 32:223-229 (1987); Gleason, J. G., et al., *J. Med. Chem.* 30:959-961 (1987)). When taken together, the findings that LXA$_4$ (1) blocks the binding of [$^3$H]-LTD$_4$, (2) effects the generation of IP$_3$, and (3) is antagonized by a well-defined LTD$_4$ receptor antagonist (e.g., SKF 104353) establish the involvement of a common recognition site in mediating the actions of these two eicosanoids on mesangial cells.

EXAMPLE 3

Physiologic Interactions of LTD$_4$ and LXA$_4$

Renal function was measured in vivo in Inactin-anesthetized male Munich-Wistar rats weighing 220-240 gms which were surgically prepared according to protocols described previously (Badr, K. F., et al., *Am. J. Physiol.* 22:F239-F243 (1987)). Inulin and para-aminohippurate (PAH) clearances Were used to measure GFR and effective RPF. A needle was placed at the take-off of the left renal artery through which a maintenance infusion of 0.9% NaCl at a rate of 0.05 ml/min was initiated. This infusion originated from two separate pumps each delivering at 0.025 ml/min and connected to the renal arterial catheter by means of a three-way connector. Homologous rat plasma was administered intravenously according to a protocol shown previously to maintain euvolemia (Badr, K. F., et al., *Am. J. Physiol.* 22:F239-F243 (1987)). Intra-renal arterial administration of LTD$_4$ (1 μg/kg/min) results in systemic hemodynamic alterations identical to those previously reported for LTC$_4$ (Badr, K. F., et al., *Am. J. Phvsiol.* 22:F239-F243 (1987); Badr, K. F., et al., *Circ. Res.* 54:492-499 (1984)) which included an elevation in systemic arterial pressure and a progressive loss of plasma volume. In order to minimize the systemic effects of LTD$_4$ and allow for adequate assessment of renal functional parameters, the rate of infusion of homologous rat plasma was increased upon starting LTD$_4$ and approximately 4-5 ml of plasma were administered throughout the LT infusion. The degree of change in hematocrit varied with the dose of LTD$_4$ (Table 1). Inulin and PAH concentrations were determined according to Fuhr et al. (Führ, J., *Klin. Wochhenschr.* 33:729-499 (1955)) and Smith et al. (Smith, H. W., et al., *J. Clin. Invest.* 24:388-391 (1945)). Two experimental groups Group I (n=14). First period: Clearances were performed during vehicle infusion. Second period: Measurements were repeated during a 20-minute infusion of LTD$_4$ delivered through one of the infusion pumps into the left renal artery at doses of 0.5 (n=4), 7 (n=3), 14 (n=3), and 20 (n=4) μg/kg/min.

Group II (n=12). First period: Clearances were performed during vehicle infusion. Second period: Measurements were repeated during a 20-min infusion of LXA$_4$ as in the second period, LTD$_4$ infusion was initiated through the second pump again in doses of 0.5 (n=3), 7 (n=3), 14 (n=3), and 20 (n=3) μg/kg/min (as in Group I).

TABLE 1

| | | AP (mmHg) | Hct (Vol./dl) | RPF | GFR ml/min |
|---|---|---|---|---|---|
| GROUP I | | | | | |
| CONTROL [Period 1] | A (n = 4) | 118 ± 8 | 46.3 ± 0.7 | 4.35 ± 0.17 | 1.11 ± 0.02 |
| | B (n = 3) | 110 ± 5 | 45.3 ± 2.2 | 4.53 ± 0.13 | 1.15 ± 0.10 |
| | C (n = 3) | 124 ± 3 | 49.4 ± 1.0 | 4.33 ± 0.12 | 1.08 ± 0.03 |
| | D (n = 4) | 112 ± 4 | 46.1 ± 0.8 | 4.45 ± 0.08 | 1.12 ± 0.04 |
| LTD$_4$ [Period 2] | A | 127 ± 9* | 48.3 ± 1.2 | 3.41 ± 0.50 | 0.81 ± 0.11 |
| | B | 124 ± 6* | 53.0 ± 1.5* | 2.76 ± 0.59* | 0.84 ± 0.15* |
| | C | 148 ± 5* | 59.2 ± 2.2* | 1.51 ± 0.44* | 0.32 ± 0.10* |
| | D | 128 ± 4* | 55.0 ± 1.8* | 1.20 ± 0.15* | 0.34 ± 0.80* |
| Group II | | | | | |
| CONTROL [Period 1] | A (n = 3) | 116 ± 6 | 43.7 ± 0.9 | 4.37 ± 0.04 | 1.02 ± 0.05 |
| | B (n = 3) | 115 ± 1 | 45.3 ± 0.9 | 4.29 ± 1.09 | 0.94 ± 0.10 |
| | C (n = 3) | 129 ± 3 | 44.0 ± 0.7 | 4.15 ± 0.30 | 1.00 ± 0.20 |
| | D (n = 3) | 110 ± 2 | 45.2 ± 0.1 | 3.98 ± 0.45 | 1.08 ± 0.05 |
| LXA$_4$ ]Period 2] | A | 121 ± 4 | 43.7 ± 0.9 | 4.50 ± 0.08 | 1.20 ± 0.20 |
| | B | 120 ± 0 | 44.7 ± 1.2 | 4.76 ± 0.83* | 0.98 ± 0.06 |
| | C | 127 ± 2 | 45.2 ± 0.7 | 4.87 ± 0.10* | 1.30 ± 0.10* |
| | D | 108 ± 3 | 44.5 ± 0.3 | 4.58 ± 0.20* | 1.27 ± 0.04* |
| LXA$_4$ + LTD$_4$ [Period 3] | A | 126 ± 3 | 44.3 ± 2.6 | 3.60 ± 0.43 | 1.08 ± 0.15 |
| | B | 130 ± 4 | 50.3 ± 0.7 | 2.94 ± 0.44 | 0.88 ± 0.18 |
| | C | 147 ± 7 | 51.2 ± 1.0 | 2.40 ± 0.32 | 0.74 ± 0.20 |
| | D | 131 ± 3 | 54.0 ± 1.7 | 1.58 ± 0.30 | 0.65 ± 0.10 |

Figure 3A:
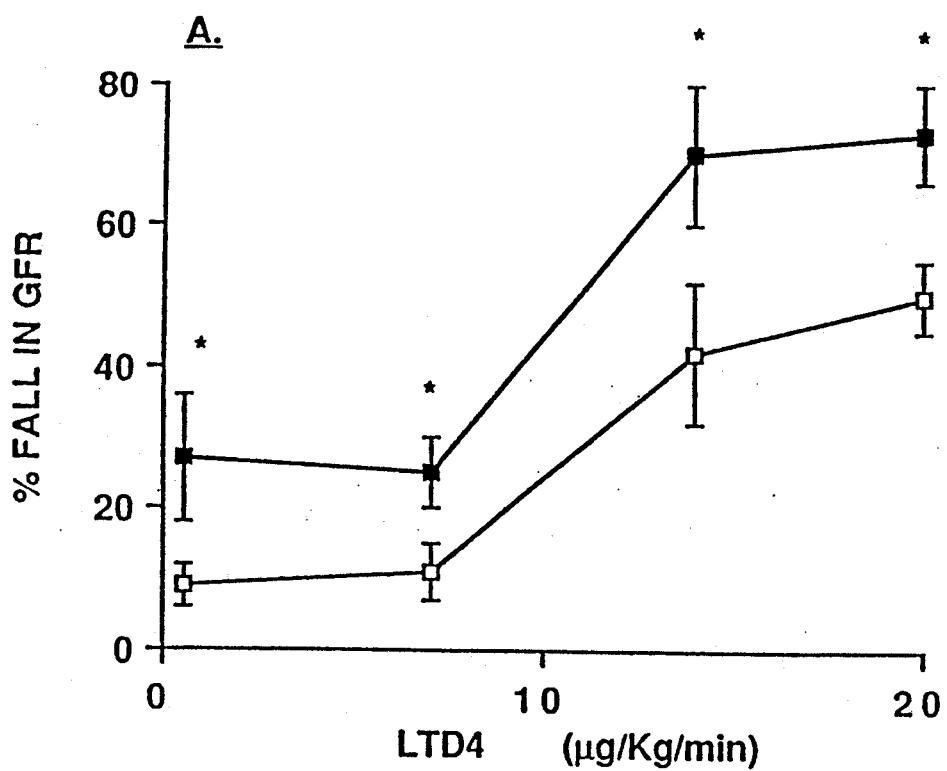
FIG. 3 is a plot of the percent reduction in glomerular filtration rate (GFR, panel A) and renal plasma flow (RPF, panel B) in response to increasing doses on intrarenal arterial $LTD_4$ without (filled squares) and with (open squares) $LXA_4$. See Table 1 for mean absolute values. *, $P,0.05$ versus corresponding points in the presence of $LXA_4$.

Administration of LTD$_4$ [LTD$_4$ doses: 0.5, 7.0, 14.0, and 20.0 (μg/kg/min)] in Group I animals was associated with dose-dependent reductions in the mean value for GFR and RPF which are summarized in Table 1. In Group II animals, administration of LXA$_4$ was associated with moderate increases in both GFR (glomerular filtration rate) and RPF (renal plasma flow) in all animals (Table 1). These responses to LTD$_4$ and LXA$_4$ were as expected from previously reported studies (Badr, K. F., et al., *Am J. Physiol.* 22:F239-F243 (1987); Badr, K. F., et al., *Biochem. Bioohvs. Res. Comm.* 145:408-414 (1987); Badr, K., et al., *Circ. Res.* 54:492-499 (1984)). The administration of increasing doses of LTD$_4$ in the presence of LXA$_4$, however (Group II, third period), was associated with marked blunting of the LTD$_4$-provoked reduction in GFR (period 2 as compared to period 3), but was without effect on OTD$_4$-induced falls in RPF (Table 1). Mean percent falls in GFR/RPF during LTD$_4$ administration were 27*/24, 25*/40*, 70*/65*, and 73*/70* at the above doses, respectively (* p<0.05 vs baseline). In the presence of LXA$_4$, these values were: 9/20*, 11/37*, and 42*/51*, and 50*/68*. The dose-response curves for LTD$_4$-induced falls in GFR and RPF in the absence and presence of LXA$_4$ are depicted in FIG. 3.

Figure 3B:
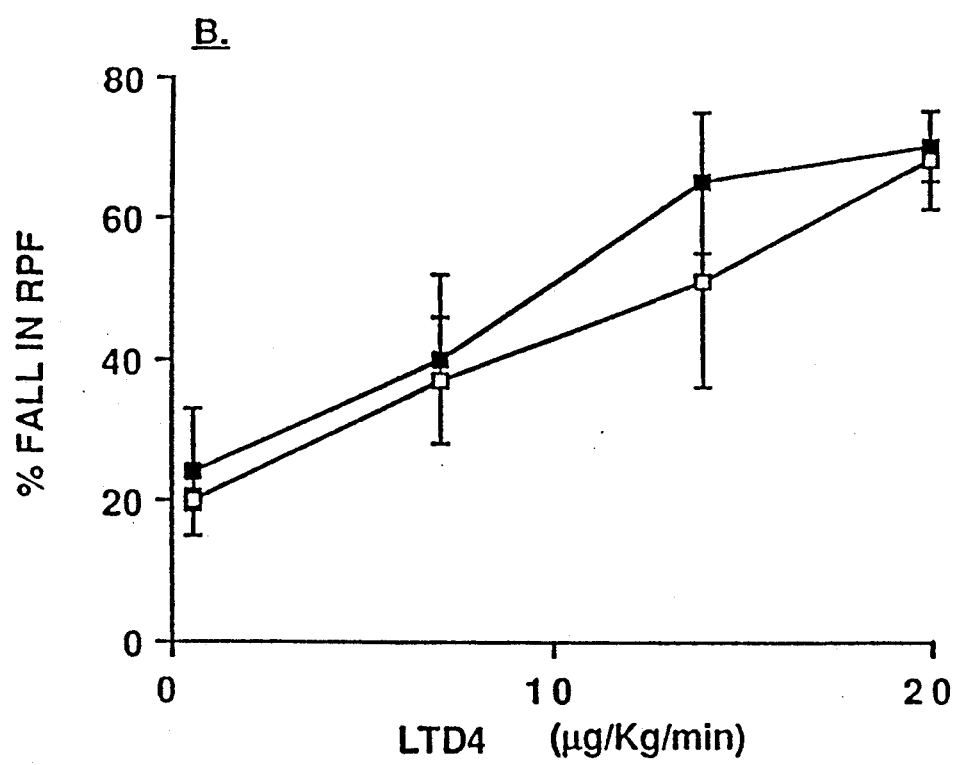

In previous studies utilizing micropuncture techniques, we defined the glomerular microcirculatory responses to both LTD$_4$ (Badr, K. F., et al., *Am. J. Phvsiol.* 22:F239-F243 (1987)) and LXA$_4$ (Badr, K. F., et al., *Biochem. Biophys. Res. Comm.* 145:408-414 (1987)) in the Munich-Wistar rat. While LTD$_4$ is a renal vasoconstrictor, the principal mechanism through which it leads to a reduction in GFR is its potent K$_f$-lowering action, resulting from mesangial cell contraction (Badr, K. F., et al., *Am. J. Phvsiol.* 22:F239-F243 (1987)). These effects of LTD$_4$ on glomerular perfusion and function are evidenced by the dose-response curves established for this eicosanoid in Group I rats (FIG. 3). The vasodilatory and GFR-augmenting effects of LXA$_4$ (Badr, K. F., et al., *Biochem. Bioohys. Res. Comm.* 145:408–414 (1987)), on the other hand, are evident in the changes in GFR and RPF seen in Group II animals (Period 2 vs. Period 1). The subsequent administration of LTD$_4$ in these rats during the continued infusion of LXA$_4$, however, is associated with a dramatic shift in the dose-response for the LTD$_4$-induced falls in GFR (Period 2 to Period 3 in Group 2 rats). The relative protection against the GFR-depressant action of LTD$_4$ (which is provided by LXA$_4$), despite absence of any modification of LTD$_4$'s potent vasoconstrictor action (FIG. 3B), is interpreted as LXA$_4$-mediated prevention of LTD$_4$-induced fall in Kf. Although it is conceivable that the afferent arteriolar dilatory action of LXA$_4$ may have augmented intraglomerular capillary pressure (PGC), and hence increased GFR, the elevated values of PGC observed during LTD$_4$ infusion (Badr, K. F., et al., *Am. J. Phvsiol.* 22:F239–F243 (1987)) argues against further elevations in this parameter as a mechanism for the observed preservation of GFR. It is possible, however, that as yet undefined actions of LXA$_4$ may play some role in the in vivo experiments. Nevertheless, these in vivo observations lend strong support to our in vitro studies demonstrating competition for LXA$_4$ for the LTD$_4$ mesangial cell receptor and its inhibition of LTD$_4$-induced IP$_3$ formation in these cells. They also provide a basis for possible relevance of LT/LX interactions in the regulation of glomerular function, particularly during inflammatory injury (Badr, K. F., et al., *J. Clin. Invest.* 81:1702–1709 (1988)).

In summary, we have shown that LXA$_4$ can displace LTD$_4$ from its binding site on rat glomerular mesangial cells and block LTD$_4$-induced IP$_3$ formation, as well as offset the physiological contractil of LTD$_4$ on these cells in vivo. Together these findings suggest that LXA$_4$, a product of human leukocytes, may regulate the actions of the peptidoleukotrienes in vivo.

Having now fully described this invention, it will be understood by those with skill in the art that the invention may be performed within a wide and equivalent range of conditions, parameters, and the like without affecting the spirit or scope of the invention or any embodiment thereof.

What is claimed is:

1. A method for antagonizing a renal response to a sulfidopeptide leukotriene in an animal wherein said method comprises administering a composition comprising a LTD$_4$-antagonist effective amount of LXA$_4$ or an active derivative thereof to said animal, wherein said active derivative is selected from the group consisting of a covalent substitution at one or more of the three hydroxyl groups of LXA$_4$ and the terminal carboxyl group of LXA$_4$ and wherein said covalent substitution is selected from the group consisting of an acetate, methyl and n-butylboronate substitution at one or more of the three hydroxyl groups of LXA$_4$ and esterification of the carboxyl group of LXA$_4$.

2. The method of claim 1, wherein said leukotriene is selected from the group consisting of LTC$_4$ and LTD$_4$.

3. The method of claim 2, wherein said leukotriene is LTD$_4$.

4. The method of claim 1, wherein said renal response to said leukotriene is a change in a renal parameter, and wherein said renal parameter is selected from the group consisting of vasoconstriction, glomerular filtration rate, renal plamsa flow, glomerular function, inositol triphosphate formation and contractile activity of renal cells.

5. The method of claim 4, wherein said renal response to said leukotriene is associated with a medical disorder selected from the group consisting of asthma, anaphylactic reactions, allergic reactions, shock, inflammation, rheumatoid arthritis, gout, psoriasis, allergic rhinitis, adult respiratory distress syndrome, Crohn's disease, endotoxin shock, traumatic shock, hemmorrhagic shock, bowel ischemic shock, renal glomerular disease, benign prostatic hypertrophy, inflammatory bowel disease, myocardial ischemia, myocardial infarction, circulatory shock, brain injury, systemic lupus erythematosus, chronic renal disease, cardiovascular disease and hypertension.

6. The method of claim 4, wherein said renal response is a change in vasoconstriction.

7. The method of claim 5, wherein said medical disorder is chronic renal disease.

8. The method of claim 5, wherein said medical disorder is an anaphylactic reaction.

9. The method of claim 5, wherein said medical disorder is an allergic reaction.

10. The method of claim 5, wherein said medical disorder is renal glomerular disease.

11. The method of claim 5, wherein said medical disorder is systemic lupus erythematosus.

12. The method of claim 5, wherein said medical disorder is hypertension.

13. The method of claim 1, wherein said effective amount is about 0.1 to about 10 mg/kg body weight/day.

14. The method of claim 13, wherein said effective amount is about 0.5 to 5 mg/kg body weight/day.

15. The method of claim 1, wherein said composition is administered parenterally, orally, or topically.

16. The method of claim 15, wherein said parenteral administration is selected from the group consisting of subcutaneous, intravenous, and intraarterial administration.

17. The method of claim 15, wherein said topical administration is selected from the group consisting of rectal and aerosol administration.

18. The method of claim 4, wherein said renal response is a change in the glomerular filtration rate.

19. The method of claim 4, wherein said renal response is a change in the renal plasma flow.

20. The method of claim 4, wherein said renal response is glomerular function.

21. The method of claim 4, wherein said renal response is a change in inositol triphosphate formation.

22. The method of claim 4, wherein said renal response is a change in contractile activity of renal cells.

* * * * *